United States Patent [19]

Higa

[11] Patent Number: 5,683,665

[45] Date of Patent: *Nov. 4, 1997

[54] COMPOSITION AND PROCESS FOR CLEANSING EXHAUST GAS

[76] Inventor: Teruo Higa, 509, Aza Shimashi, Ginowan-Shi, Okinawa-Ken, Japan

[*] Notice: The term of this patent shall not extend beyond the expiration date of Pat. No. 5,521,131.

[21] Appl. No.: 585,234

[22] Filed: Jan. 11, 1996

Related U.S. Application Data

[62] Division of Ser. No. 263,461, Jun. 22, 1994, Pat. No. 5,521,131.

[30] Foreign Application Priority Data

Jun. 25, 1993 [JP] Japan ..................... 5-204391

[51] Int. Cl.$^6$ ............... C04B 33/00; C10K 1/32; C10K 3/00
[52] U.S. Cl. ............. 423/212; 423/210; 423/215.5; 423/246; 423/247; 501/94; 501/141; 502/80; 502/60; 55/DIG. 30; 55/523; 95/45; 95/274; 95/902; 435/266; 422/168
[58] Field of Search ................... 501/1, 94, 141, 501/81; 502/60, 80; 423/212, 246, 247, 215.5, 210; 95/45, 51, 273, 274, 902; 55/DIG. 30, 523; 435/266; 422/168

[56] References Cited

U.S. PATENT DOCUMENTS

| | | | |
|---|---|---|---|
| 5,008,220 | 4/1991 | Brown | 501/81 |
| 5,132,255 | 7/1992 | Takeuchi | 501/141 |
| 5,296,180 | 3/1994 | Hayes | 264/44 |
| 5,521,131 | 5/1996 | Higa | 501/141 |

FOREIGN PATENT DOCUMENTS

| | | |
|---|---|---|
| 304854 | 4/1918 | Germany. |
| 0375256 | 3/1991 | Japan. |

OTHER PUBLICATIONS

Kromer et al. "Refinement & Enrichment of Clay . . . " Proceedings of the International Conference on Science on Ceramics, vol. 14, 1988, London, G.B., pp. 113–118 (no month).

Chemical Abstracts, 142624n, vol. 106, No. 18, May 1987 Columbus, Ohio, p. 274, TR. Inst. Mosk.

Khim–Tekhnol. . Inst. Im D.I. Mendeleeva, vol. 137, 1985 Moscow UDSSR, pp. 66–72, V.V. Baranov. et al. (no month).

*Primary Examiner*—Michael Marcheschi
*Attorney, Agent, or Firm*—Ladas & Parry

[57] ABSTRACT

According to the present invention, ceramics which are prepared by calcining a composition comprising raw ceramic materials and a microorganism and/or culture fluid thereof, wherein the microorganisms is capable of producing an antioxidation material. The ceramic of the present invention possesses a variety of activities of, for instance, improving the soil, decomposing sewage or sludge, and deodorizing an unpleasant odor.

6 Claims, No Drawings

COMPOSITION AND PROCESS FOR CLEANSING EXHAUST GAS

This is a divisional of application Ser. No. 08/263,461 filed on Jun. 22, 1994 U.S. Pat. No. 5,521,131.

BACKGROUND OF THE INVENTION

1. Field of the Invention

The present invention relates to a functional ceramic having a wide variety of biological activities and a process for preparing the same.

2. Related Art

Ceramics possessing biological activities are known in the art.

For instance, functional ceramics provided with activities by controlling the internal physical structure, by calcining with materials having catalytic functions, or by adsorbing microbes or catalysts into the pores of porous ceramics have been proposed.

However, most of the conventional functional ceramics, in general, have a single activity to be aimed. Further, the activity is sometimes insufficient and may be lost with the passage of time. Particularly, the ceramics provided with the activity by adsorbing microorganisms or catalysis, further improvements are desired in some points. For instance, in the ceramics the density of microorganisms may vary with the lapse of time. Moreover, the activity of ceramics may not be stable, unless environmental conditions, such as pH or temperature are maintained constant.

SUMMARY OF THE INVENTION

Therefore, the object of the present invention is to provide a functional ceramic which possess a wide variety of activities and are stable and used for a long period of time.

According to the present invention, there provides a ceramic obtainable by calcining a composition comprising raw ceramic materials and a microorganism and/or culture fluid thereof, wherein the microorganism is capable of producing an antioxidation material.

According to the present invention, there also provides a process for preparing a ceramic, comprising calcining a ceramic material with a microorganism and/or culture fluid thereof, wherein the microorganism is capable of producing an antioxidation material.

DETAILED DESCRIPTION OF THE INVENTION

Ceramic

The functional ceramic according to the present invention are obtainable by calcining composition raw ceramic materials and a specific microorganism and/or a culture thereof.

The microorganism employed in the present invention is capable of producing an antioxidation material. The term "antioxidation material" herein means a material suppressing the oxidation of iron or a material decomposing or resolving an active oxygen. The antioxidation material includes, for examples, a variety of organic acids, amino acids and proteins.

Preferable specific examples of the microorganisms include:

the microorganisms belonging to actinomycetes include those belonging to genera Streptomyces, Streptoverticillium, Nocardia, Micromonospora and Rhodococcus. Specific examples of actinomycetes include *Streptomyces albus* (e.g. ATCC 3004), *Streptoverticillium baldaccii* (e.g. ATCC 23654), *Nocardia asteroides* (e.g. ATCC 19247), *Micromonospora chalcea* (e.g. ATCC 12452) and *Rhodococcus rhodochrous* (e.g. ATCC 1380);

the microorganisms belonging to photosynthetic bacteria include those belonging to genera Rhodopseudomonas, Rhodospirillum, Chromatium and Chlorobium. Specific examples of photosynthetic bacteria include *Rhodopseudomonas sphaeroides* (e.g. IFO 12203), *Rhodospirillum rubrum* (e.g. IFO 3986), *Chromatium okenii* and *Chlorobium limicola*;

the microorganisms belonging to lactic acid bacteria include those belonging to genera Lactobacillus, Propionibacterium, Pediococcus and Streptococcus. Specific examples of lactic acid include *Lactobacillus bulgaricus* (e.g. ATCC 11842), *Propionibacterium freudenreichii* (e.g. IFO 12391), *Pediococcus halophilus* (e.g. IFO 12172), *Streptococcus lactis* (e.g. IFO 12007) and *Streptococcus faecalis* (e.g. IFO 3971);

the microorganisms belonging to mold fungi include those belonging to genera Aspergillus and Mucor. Specific examples of mold fungi include *Aspergillus japonicus* (e.g. IFO 4060), *Aspergillus oryzae* (e.g. IFO 4075) and *Mucor hiemalis* (e.g. IFO 5303); and the microorganisms belonging to yeast include those belonging to genera Saccharomyces and Candida. Specific examples of yeast include *Saccharomyces cerevisiae* (e.g. IFO 0304), *Saccharomyces lactis* (e.g. IFO 0433) and *Candida utilis* (e.g. IFO 0396).

According to the preferred embodiment of the present invention, a plural of the microorganisms are employed. The microorganisms are preferably selected from each of five groups of actinomycetes, phototrophic bacteria, lactic acid bacteria, mold fungi and yeast.

These microorganisms may be cultured under the conventional culture condition of microorganisms.

The microorganisms and/or culture products thereof (the term "culture fluid" will mean hereinafter the microorganism and/or culture products thereof) are added to raw ceramic materials, which are then calcined to give ceramic.

The raw ceramic materials herein means materials which can be calcined to produce ceramic and includes those usually used in the production of ceramics. Specific examples of the raw ceramic materials include clay, zeolite, bakuhan-seki and the other materials of porcelains such as kaolin, gainome-clay, kibushi-clay, pottery stone, feldspar. These ceramic materials may be used alone or as a mixture of the two or more. In view of the physical properties, such as strength, of ceramic to be finally obtained, the raw ceramic materials are preferably those of which the components are controlled.

Preferable specific examples of the clay include Akatsu-gaimome-clay (Aichi, Japan, Silicate: 50.14%, Titanium oxide: 0.50%, Alumina: 34.70%, Iron oxide: 1.36%, Lime: 0.24%, Magnesia: 0.10%, Potassium oxide: 0.56%, Sodium oxide: 0.30%), Tokikuchi-gaimome-clay (Gifu, Japan, Silicate: 47.51%, Titanium oxide: 0.46%, Alumina: 36.60%, Iron oxide: 1.24%, Lime: 0.22%, Magnesia: 0.21%, Potassium oxide: 0.60%, Sodium oxide: 0.04%), Shimagahara-gaimome-clay (Mie, Japan, Silicate: 48.14%, Titanium oxide: 1.03%, Alumina: 35.01%, Iron oxide:1.17%, Lime: 0.54%, Magnesia: 0.28%, Potassium oxide: 0.44%, Sodium oxide: 0.40%), Motoyama-kibushi-clay (Aichi, Japan, Silicate: 45.48%, Titanium oxide: 0.62%, Alumina: 32.15%, Iron oxide: 0.74%, Lime: 0.29%, Magnesia: 0.24%, Potassium oxide: 0.54%, Sodium oxide: 0.19%), Hara-kibushi-clay (Gifu, Japan, Silicate: 51.88%, Alumina: 33.07%, Iron oxide: 1.83%, Lime: 0.42%, Magnesia: 0.25%, Potassium oxide: 0.92%, Sodium oxide: 0.17%), and Shimagahara-kibushi-clay (Mie, Japan, Silicate: 49.78%, Titanium oxide: 0.90%, Alumina: 29.74%, Iron oxide: 2.07%, Lime: 0.24%, Magnesia: 0.03%, Potassium oxide: 0.23%, Sodium oxide: 0.38%, Water: 15.76%).

The ceramic materials are preferably dried beforehand and passed through a screen so that the materials has an appropriate range of the particle size distribution.

The amount of the culture fluid to be added to the raw ceramic material are preferably in the range of 25 to 40% by weight.

The culture fluid and the ceramic material and, if necessary, a binder as well as a variety of additives are added simultaneously or in an appropriate sequence, and blended satisfactorily with an appropriate mixing means.

The blend thus obtained is next molded. The shape of the ceramic according to the present invention is not particularly limited and may be made adapted to various applications described hereunder.

The blend thus molded is preferably dried and calcined.

Calcination temperature of the blend is preferably in the range of 700° to 1300° C., particularly 700° to 1050° C. The blend is preferably calcined for 4 to 15 hours. After the calcination, the ceramic are cooled to give the functional ceramic according to the present invention.

Uses of ceramic

The ceramic according to the present invention have a wide variety of biological activities. Without intending to be bound by theory, it is believed that something derived from the microorganisms remains in the ceramic and provides biological activities with ceramic even after the calcination.

The ceramic according to the present invention has an activity of improving the soil. Therefore, according to another aspect of the present invention, there provides a composition for improving the soil comprising the ceramic of the present invention as an active ingredient. There also provides a method for improving the soil comprising the step of applying the ceramic of the present invention to the soil. According to the preferred embodiment of the present invention, the ceramic which is in the form of particles may apply the soil. The amount of the ceramic applied is preferably in the range of 25 to 100 g per 1 m$^2$ of the soil.

Further, the ceramic according to the present invention has an activity of improving water quality or decomposing sewage or sludge, i.e., an aqueous solution. Therefore, according to a further aspect of the present invention, there provides a composition for improving water quality or decomposing sewage or sludge comprising the ceramic of the present invention as an active ingredient. There also provides a method for improving water quality or decomposing sewage or sludge comprising the step of bringing the ceramic of the present invention into contact with sewage or sludge. When used for improving water quality or decomposing sewage or sludge, the ceramic of the present invention, preferably in the form of particles, may be spread over the bottom of a container in which waste water are contained or may be put in a bag and immersed in the container. Alternatively, a fine powdery ceramic of the present invention may be coated on a surface of the container.

The ceramic of the present invention also has an activity of deodorizing an odor. Therefore, according to another aspect of the present invention, there provides a composition for deodorizing the odor comprising the ceramic of the present invention as an active ingredient. There also provides a method for deodorizing the odor comprising the step of bringing the ceramic of the present invention in contact with the source of the odor. According to the preferred embodiment of the present invention, the amount of the ceramic used for the deodorization is preferably in the range of 1 to 15 g/kg of the source of the odor such as garbage and wastes. Alternatively, it is also possible to prepare a bag having an activity of deodorizing the odor. The bag may be prepared by blending the powdery functional ceramic with paper manufacturing materials or plastic materials, preparing paper or plastic film with the paper materials or plastic materials, and preparing a bag made of the paper or the plastic film thus obtained.

The ceramic of the present invention has an activity of improving fuels, such as gasoline. Therefore, according to another aspect of the present invention, there provides a composition for improving the fuel comprising the ceramic of the present invention as an active ingredient. There also provides a method for improving the fuel comprising the step of bringing the fuel into contact with the ceramic of the present invention.

The ceramic of the present invention has an activity of reducing harmful component levels in an exhaust gas. Therefore, according to a further aspect of the present invention, there provides a composition for treating the exhaust gas to reduce harmful component levels in the exhaust gas, comprising the ceramic of the present invention as an active ingredient. There also provides a method for cleaning up the exhaust gas comprising the step of bring the exhaust gas into contact with the ceramic of the present invention. According to the preferred embodiment of the present invention, the ceramic of the present invention may be put in an exhaust pipe of a car or motorcycle.

The invention is illustrated in more detail by reference to the following examples.

EXAMPLE 1

Preparation of ceramic

Each of the culture fluids of *Streptomyces albus* (ATCC 3004), *Streptoverticillium baldaccii* (ATCC 23654), *Nocardia asteroides* (ATCC 19247), *Micromonospora chalcea* (ATCC 12452), *Rhodopseudomonas sphaeroides* (IFO 12203), *Rhodospirillum rubrum* (IFO 3986), *Lactobacillus bulgaricus* (IFO 3986), *Propionibacterium freudenreichii* (IFO 12391), *Pediococcus halophilus* (IFO 12172), *Streptococcus lactis* (IFO 12007), *Streptococcus faecalis* (IFO 3971), *Aspergillus Japonicus* (IFO 4060), *Aspergillus oryzae* (IFO 4075), *Mucor hiemalis* (IFO 5303), *Saccharomyces cerevisiae* (IFO 0304), *Saccharomyces lactis* (IFO 0433), *Candida utilis* (IFO 0396) cultured in 4% molasses solution was prepared and blended in an amount of 20–35% by weight with Gaimome-clay. The blend was sufficiently kneaded, formed into particles. The particles were dried and calcined at 700° C. for 6 hours to give ceramic particles (particle diameter: 2–3 mm).

COMPARATIVE EXAMPLE

Ceramic without fluid of microorganisms

Ceramic particles were prepared in the same manner as that of Example 1 except that the culture fluid of the microorganism was not added.

EXAMPLE 2

Improvement of soil

The particles of the ceramic obtained in Example 1 was applied in an amount of 50 g per 1 m² of the soil. Then, spinach, SANTOSAI (a greenstuff), and chiboul were cultured. Results are shown in Table 1. Culture in the soil with the ceramic of the present invention brought about the increased harvest in 10 to 20% or more as compared with the harvest in the soil without the ceramic.

TABLE 1

Effect of functional ceramic on harvests of vegetables

|  | Treated Area | | Non-treated Area | |
| --- | --- | --- | --- | --- |
| Product | Height (cm) | Harvest/m² (kg) | Height (cm) | Harvest/m² (kg) |
| Spinach | 35 | 4.5 | 33 | 3.8 |
| SANTOSAI | 32 | 4.6 | 30 | 4.0 |
| Chiboul | 45 | 5.4 | 43 | 4.6 |

EXAMPLE 3

Water quality improvement (1)

The ceramic particles obtained in Example 1 were spread with a thickness of about 1 cm over the bottom of a 50 liter container in which waste water (BOD, 280 ppm; SS, 120 ppm) was contained. The change in the water quality of the waste water was observed. Also, the change in the water quality was observed in the case that the ceramic obtained in Comparative Example were spread. The results are shown in Table 2.

TABLE 2

Water quality improvement

| Ceramic | | Before treatment | After | | | | |
| --- | --- | --- | --- | --- | --- | --- | --- |
| | | | 1day | 3days | 5days | 7days | 9days |
| Example 1 | BOD | 280 | 75 | 20 | 5 | 3 | 3 |
| | SS | 120 | 50 | 10 | 4 | 4 | 2 |
| Comparative | BOD | 280 | 230 | 200 | 183 | 151 | 140 |
| Example | SS | 120 | 110 | 98 | 81 | 64 | 60 |

BOD: Biological Oxygen Demand (ppm),
SS: Suspended Substance (ppm).

EXAMPLE 4

Water quality improvement (2)

The ceramic particles obtained in Example 1 were processed in the form of powder. A concrete bath which was not cured was prepared. The powder was coated on the surface of the bath. And then, the bath was cured. The concrete bath was filled with waste water. Changes in water quality was observed. The results are shown in Table 3.

TABLE 3

Purification of water

| Ceramic | | Before treatment | After | | | | |
| --- | --- | --- | --- | --- | --- | --- | --- |
| | | | 1day | 3days | 5days | 7days | 9days |
| Example 1 | BOD | 50 | 43 | 21 | 13 | 6 | |
| | SS | 10 | 7 | 5 | 3 | 2 | |
| Comparative | BOD | 50 | 48 | 45 | 44 | 41 | |
| Example | SS | 10 | 9 | 9 | 8 | 7 | |

BOD: Biological Oxygen Demand (ppm),
SS: Suspended Substance (ppm).

EXAMPLE 5

Water quality improvement (3)

The ceramic particles obtained in Example 1 were charged as a filter in a filtering apparatus having a capacity of 300 liter/hour. Waste water used in Example 3 was introduced into the filtering apparatus. The change in the quality of the filtrate was observed.

Filtration was conducted in the same manner as the above with the ceramic obtained in Comparative Example to observe the change in the quality of filtrate.

The results are shown in Table 4.

TABLE 4

Purification of water

| Ceramic | | Before treatment | After | | |
| --- | --- | --- | --- | --- | --- |
| | | | 2 hours | 4 hours | 6 hours |
| Example 1 | BOD | 208 | 5 | 1 | 0.01 |
| | SS | 120 | 0.5 | 0 | 0 |
| Comparative | BOD | 280 | 140 | 100 | 51 |
| Example | SS | 120 | 25 | 21 | 18 |

BOD: Biological Oxygen Demand (ppm),
SS: Suspended Substance (ppm).

EXAMPLE 6

Deodorization (1)

The ceramic particles obtained in Example 1 or Comparative Example was applied in an amount of 3 g to 1 kg of garbage from households. The garbage was sealed and left to stand for 10 days. Then, concentrations of ammonia and hydrogen sulfide as the sources of unpleasant odor were measured. The results are shown in Table 5.

TABLE 5

Deodorization (1)

| Ceramic | Ammonia (ppm) | Hydrogen sulfide (ppm) | Methyl-mercaptan (ppm) | Trimethylamine (ppm) |
| --- | --- | --- | --- | --- |
| Example 1 | N.D. | N.D. | N.D. | N.D. |
| Comparative Example | 4.4 | 2.81 | 0.051 | 0.131 |

N.D.: Non-detected.

EXAMPLE 7

Deodorization (2)

The ceramic particles obtained in Example 1 were processed into powder and blended into paper manufacturing materials. Then, a paper bag was prepared from the paper manufacturing material. The paper bag was filled with garbage from households, sealed and left to stand for 10 days. Then, concentrations of the sources of the unpleasant odor such as ammonia or hydrogen sulfide were measured. The results are shown in Table 6.

TABLE 6

| | Deodorization (2) | | | |
|---|---|---|---|---|
| Ceramic | Ammonia (ppm) | Hydrogen sulfide (ppm) | Methyl-mercaptan (ppm) | Trimethyl-amine (ppm) |
| Example 1 | N.D. | N.D. | N.D. | N.D. |
| Comparative Example | 4.1 | 2.9 | 0.041 | 0.121 |

N.D.: Non-detected.

EXAMPLE 8

Deodorization (3)

The ceramic particles obtained in Example 1 or Comparative Example were processed into powder and blended in an amount of 10% into nylon material. Then, a nylon bag was prepared from the nylon material. The bag was filled with garbage from a households, sealed and left to stand for 10 days. Then, concentrations of the sources of the unpleasant odor such as ammonia or hydrogen sulfide were measured.

The results are shown in Table 7.

TABLE 7

| | Deodorization | | | |
|---|---|---|---|---|
| Ceramic | Ammonia (ppm) | Hydrogen sulfide (ppm) | Methyl-mercaptan (ppm) | Trimethyl-amine (ppm) |
| Example 1 | N.D. | N.D. | N.D. | N.D. |
| Comparative Example | 4.4 | 3.3 | 0.045 | 0.135 |

N.D.: Non-detected.

EXAMPLE 9

Decomposition of sludge

The ceramic particles obtained in Example 1 were mixed with sludge collected from the bottom of the sea. The amount of the ceramic was about 100 g into 5 liters of the sludge. The mixture was left to stand in a 10 liter clear glass bottle for 90 days. Then, the amount of sludge left in the bottle was measured.

The results are shown in Table 8.

TABLE 8

| Ceramic | Initial (liter) | 30 days (liter) | 60 days (liter) | 90 days (liter) |
|---|---|---|---|---|
| Example 1 | 5 | 4.5 | 3.9 | 3.0 |
| Comparative Example | 5 | 4.9 | 4.9 | 4.9 |

EXAMPLE 10

Improving fuel

The ceramic particles obtained in Example 1 or Comparative Example were charged as a filter in a filtering apparatus having a capacity of 300 liter/hour. A commercially available gasoline was circulated through the filtering apparatus for hours. The gasoline obtained was then supplied to a car to measure the travelling distance per fuel consumption.

The results are shown in Table 9.

TABLE 9

| | | Trial | | |
|---|---|---|---|---|
| Ceramic | | 1st | 2nd | 3rd |
| Example 1 | Travelling distance per 40 liter | 331.2 km | 328 km | 334 km |
| | Fuel expenses | 8.28 km/l | 8.2 km/l | 8.35 km/l |
| Comparative Example | Travelling distance per 40 liter | 228 km | 288 km | 288 km |
| | Fuel expenses | 7.2 km/l | 7.2 km/l | 7.2 km/l |

EXAMPLE 11

Reduction of harmful component levels in exhaust gas

A cylindrical pipe (diameter: 10–20 mm) of the ceramic of the present invention was prepare by substantially the same manner as that Example 1. The ceramic pipe thus obtained was put in an exhaust pipe of a car. The CO and HC levels in an exhaust gas was measured.

The results are shown in Table 10.

TABLE 10

| Ceramic | CO (%) | HC (ppm) |
|---|---|---|
| Example 1 | 0.02 | 0.1 |
| Comparative Example | 0.4 | 1.3 |

What is claimed is:

1. An exhaust cleansing composition comprising an effective amount of an exhaust cleansing ceramic obtained by calcining a composition comprising raw ceramic materials and 25 to 40 weight percent of microorganisms and/or culture fluid thereof at a temperature and for a time sufficient for calcination to take place, wherein at least five microorganisms are selected and at least one microorganism is selected from each of the five groups of actinomycetes, phototrophic bacteria, lactic acid bacteria, mold fungi and yeast wherein said actinomycetes belong to genus Streptomyces, Streptoverticillium, Nocardia, Micromonospora, or Rhodococcus;

said phototrophic bacteria belong to genus Rhodopseudomonas, Rhodospirillum, Chromatium or Chlorobium;

said lactic acid bacteria belong to genus Lactobacillus, Propionibacterium, or Pediococcus;

said mold fungi belong to genus Aspergillus or Mucor; and said yeast belong to genus Saccharomyces or Candida.

2. A composition according to claim 1, wherein one or more microorganisms of actinomycetes are selected from the microorganisms which belong to *Streptomyces albus, Streptoverticillium baldaccii, Nocardia asteroides, Micromonospora chalcea* or *Rhodococcus rhodochrous;* one or more microorganisms of phototrophic bacteria are selected from the microorganisms which belong to

*Rhodopseudomonas spheroids, Rhodospirillum rubrum,* or *Chlorobium limicola;* one or more microorganisms of lactic acid bacteria are selected from the microorganisms which belong to *Lactobacillus bulgaricus, Propionibacterium freudenreichii, Pediococcus halophilous, Streptococcus lactis* or *Streptococcus faecalis;* one or more microorganisms of mold fungi are selected from the microorganisms that belong to *Aspergillus japonicus, Aspergillus oryzae,* or *Mucor hiemalis;* and one or more microorganisms of yeast are selected from the microorganisms which belong to *Saccharomyces cerevisiae, Saccharomyces lactis* or *Candida utilis.*

3. A composition according to claim 1, wherein the ceramic material is selected from the group consisting of clay, zeolite and bakuhan-seki.

4. A process for cleansing an exhaust gas comprising contacting the exhaust gas with a surface of a ceramic said ceramic obtained by calcining a composition comprising raw ceramic materials and 25 to 40 weight percent of microorganisms comprising raw ceramic materials and 25 to 40 weight percent of microorganisms culture fluid thereof at a temperature and for a time sufficient for calcination to take place, wherein at least five microorganisms are selected and at least one microorganism is selected from each of the five groups of actinomycetes, phototrophic bacteria, lactic acid bacteria, mold fungi and yeast wherein said actinomycetes belong to genus Streptomyces, Streptoverticillium, Nocardia, Micromonospora, or Rhodococcus;

said phototrophic bacteria belong to genus Rhodopseudomonas, Rhodospirillum, Chromatium, or Chlorobium;

said lactic acid bacteria belong to genus Lactobacillus, Propionibacterium, or Pediococcus;

said mold fungi belong to genus Aspergillus or Mucor; and said yeast belong to genus Saccharomyces or Candida.

5. A process according to claim 4, wherein one or more microorganisms of actinomycetes are selected from the microorganisms which belong to *Streptomyces albus, Streptoverticillium baldaccii, Nocardia asteroides, Micromonospora chalcea* or *Rhodococcus rhodochrous;* one or more microorganisms of phototrophic bacteria are selected from the microorganisms which belong to *Rhodopseudomonas spheroids, Rhodospirillum rubrum,* or *Chlorobium limicola;* one or more microorganisms of lactic acid bacteria are selected from the microorganisms which belong to *Lactobacillus bulgaricus, Propionibacterium freudenreichii, Pediococcus halophilous, Streptococcus lactis* or *Streptococcus faecalis;* one or more microorganisms of mold fungi are selected from the microorganisms that belong to *Aspergillus japonicus, Aspergillus oryzae,* or *Mucor hiemalis;* and one or more microorganisms of yeast are selected from the microorganism which belong to *Saccharomyces cerevisiae, Saccharomyces lactis* or *Candida utilis.*

6. A process according to claim 4, wherein the ceramic material is selected from the group consisting of clay, zeolite and bakuhanseki.

* * * * *